United States Patent
Choi et al.

(10) Patent No.: US 7,362,123 B2
(45) Date of Patent: Apr. 22, 2008

(54) INSPECTION APPARATUS FOR THIN FILM TRANSISTOR SUBSTRATE

(75) Inventors: Ho-seok Choi, Suwon-si (KR); Sergey Antonov, Suwon-si (KR); Hyeong-min Ahn, Yongin-si (KR); Jeong-su Ha, Suwon-si (KR); Lemjachine Vassili, Suwon-si (KR); Mi-jeong Song, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 11/328,177

(22) Filed: Jan. 10, 2006

(65) Prior Publication Data

US 2006/0186335 A1   Aug. 24, 2006

(30) Foreign Application Priority Data

Jan. 31, 2005   (KR) ............... 10-2005-0008837

(51) Int. Cl.
  *G01R 31/26*   (2006.01)
  *G01R 31/302*   (2006.01)
(52) U.S. Cl. ............... 324/770; 250/306; 345/904
(58) Field of Classification Search ............... 324/770; 250/306–443.1
  See application file for complete search history.

(56) References Cited

U.S. PATENT DOCUMENTS

| 5,432,461 A * | 7/1995 | Henley ............... 324/770 |
| 6,765,203 B1 * | 7/2004 | Abel ............... 250/310 |
| 6,873,175 B2 * | 3/2005 | Toro-Lira et al. ............ 324/770 |
| 7,132,671 B2 * | 11/2006 | Hatajima ............... 250/491.1 |
| 7,157,921 B2 * | 1/2007 | Shonohara ............... 324/751 |
| 2004/0223140 A1 | 11/2004 | Shonohara |

FOREIGN PATENT DOCUMENTS

KR   1997-75840   12/1997

\* cited by examiner

*Primary Examiner*—Ha Tran Nguyen
*Assistant Examiner*—Emily Y Chan
(74) *Attorney, Agent, or Firm*—Stanzione & Kim, LLP (57) ABSTRACT

An inspection apparatus for a TFT substrate formed with a plurality of pixels, includes a reference substrate being opposite to and spaced from the TFT substrate and formed with a plurality of reference patterns corresponding to the pixels, a power supply to supply power to both a predetermined number of the pixels and the corresponding reference pattern to form an electric field in a space between the TFT substrate and the reference substrate, an electron beam emitter to emit an electron beam to travel from a first side to a second side of the space, an electron beam detector to detect the electron beam emitted from the electron beam emitter and passed through the space, and a controller to determine whether the TFT substrate includes a defective pixel based on a location of the electron beam detected by the electron beam detector. Thus, the inspection apparatus can correctly and quickly inspect the TFT substrate for defects in a low vacuum state regardless a size of the TFT substrate.

20 Claims, 5 Drawing Sheets

INSPECTION APPARATUS FOR THIN FILM TRANSISTOR SUBSTRATE

CROSS-REFERENCE TO RELATED APPLICATIONS

This application claims the benefit under 35 U.S.C. §119 from Korean Patent Application No. 2005-8837, filed on Jan. 31, 2005, in the Korean Intellectual Property Office, the disclosure of which is incorporated herein in its entirety by reference.

BACKGROUND OF THE INVENTION

1. Field of the Invention

The present general inventive concept relates to an inspection apparatus for a thin film transistor (TFT) substrate, and more particularly, to an inspection apparatus capable of inspecting a defective pixel of a TFT substrate using deflection of an electron beam.

2. Description of the Related Art

A conventional inspection apparatus for inspecting a TFT substrate includes an oscilloscope probe controlled to contact the TFT substrate to analyze a waveform of a signal output by the probe when the probe is placed in contact with the TFT substrate. It takes relatively long time when inspecting the TFT substrate with the conventional inspection apparatus having the oscilloscope probe to be in contact with the TFT substrate during inspecting because the oscilloscope probe has to be moved mechanically. Further, the TFT substrate is likely to be damaged because the oscilloscope probe directly contacts the TFT substrate.

Accordingly, a contactless inspection apparatus without using the oscilloscope probe has been developed as an alternative to the conventional inspection apparatus using the oscilloscope probe in contact with the TFT substrate. The contactless inspection apparatus uses a voltage contrast of electron, that is, emits an electron beam to a TFT substrate and then detects a secondary electron reflected from the TFT substrate, thereby inspecting defects on the TFT substrate.

For example, inspection apparatuses detecting the secondary electron have been disclosed in Japanese Patent First Publication Nos. 2000-3142 and 1999-265678.

Such a contactless inspection apparatus can detect the secondary electron beam if a vacuum chamber accommodating the TFT substrate is maintained in a high vacuum state. That is, when a plurality of TFT substrates have to be inspected, the vacuum chamber should be highly vacuumized whenever each TFT substrate is placed inside the vacuum chamber for inspection. Hence, it takes a relatively long time to highly vacuumize the vacuum chamber.

Further, because equipment for highly vacuumizing the vacuum chamber is additionally provided, a size of the contactless inspection apparatus increases correspondingly.

Also, because the electron beam emitted from an electron gun is perpendicular to the surface of the TFT substrate, the position of the electron beam relative to the TFT substrate should be changed according to the size of the TFT substrate, since the TFT substrates may have different sizes.

SUMMARY OF THE INVENTION

The present general inventive concept provides an inspection apparatus capable to correctly and quickly inspect a defect of a TFT substrate in a low vacuum state regardless of a size of the TFT substrate.

Additional aspects and/or advantages of the present general inventive concept will be set forth in part in the description which follows and, in part, will be obvious from the description, or may be learned from the practice of the present general inventive concept.

The foregoing and/or other aspects of the present general inventive concept may be achieved by providing an inspection apparatus for a TFT substrate formed with a plurality of pixels, the inspection apparatus comprising a reference substrate spaced apart from the TFT substrate and formed with a plurality of reference patterns corresponding to the pixels, a power supply to supply power to both a predetermined number of the plurality of pixels and at least one of the reference patterns corresponding to the predetermined number of the plurality of pixels to form an electric field in a space between the TFT substrate and the reference substrate, an electron beam emitter to emit an electron beam to travel from a first side to a second side of the space, an electron beam detector to detect the electron beam emitted from the electron beam emitter after passing through the space, and a controller to determine whether the TFT substrate includes a defective pixel based on a detected location of the electron beam detected by the electron beam detector.

The electron beam emitter may further include a plurality of micro electron guns arranged on the first side of the space along a surface of the TFT substrate to respectively emit electron beams, and a plurality of focusing units to focus the electron beams emitted from the corresponding micro electron guns, respectively, and the controller controls the focusing units to focus the electron beams emitted from the respective micro electron guns to pass between one of pixel lines formed by the predetermined number of the plurality of pixels of the TFT substrate and a line of reference patterns corresponding to the pixel line.

The controller may control the power supply to selectively supply power to at least one of the plurality of reference patterns of the reference substrate.

The controller may have information about a reference detection location when the TFT substrate includes no defective pixel, and determines whether the TFT substrate includes the defective pixel based on a deviation between the reference detection location and the location of the electron beam detected by the electron beam detector.

The inspection apparatus may further include a substrate stage on which the TFT substrate is placed to be opposite to and spaced from the reference substrate, a vacuum chamber to accommodate the reference substrate, the electron beam detector and the substrate stage, and a chamber vacuumizer to vacummize the vacuum chamber 70 according to control of the controller.

The foregoing and other aspects of the present general inventive concept may also be achieved by providing an inspection apparatus to identify a defect on a TFT substrate, the inspection apparatus comprising an electron beam emitter to emit at least one electron beam toward a space between the TFT substrate and a reference substrate, and an electron beam detector to detect a location of the at least one electron beam passing through the space, and to detect a defective pixel of the TFT substrate according to the detected location of the at least one electron beam.

The foregoing and/or other aspects of the present general inventive concept may be achieved by providing a method of identifying a defect on a TFT substrate using an electron beams in an inspection apparatus, the method comprising supplying an electric field between a pixel line of the TFT substrate and a reference line of a reference substrate, directing the electron beam across the electric field, detecting a location of the electron beam after passing through a space between the TFT substrate and the reference substrate, and identifying a defect on the TFT substrate based on a deviation of the detected location from a reference detection position.

BRIEF DESCRIPTION OF THE DRAWINGS

These and other aspects and advantages of the present general inventive concept will become apparent and more readily appreciated from the following description of the embodiments, taken in conjunction with the accompany drawings of which.

DETAILED DESCRIPTION OF THE PREFERRED EMBODIMENTS

Reference will now be made in detail to the embodiments of the present general inventive concept, examples of which are illustrated in the accompanying drawings, wherein like reference numerals refer to like elements throughout. The embodiments are described below so as to explain the present general inventive concept by referring to the figures.

Figure 1:
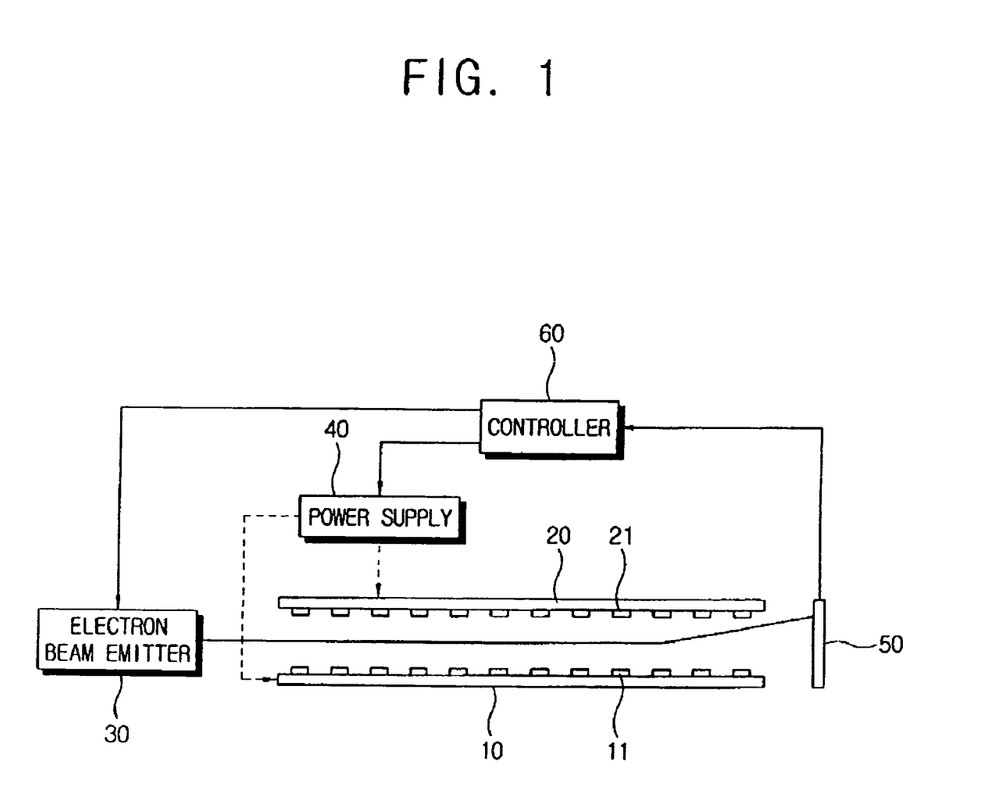
FIG. 1 illustrates an inspection apparatus according to an embodiment of the present general inventive concept.

FIG. 1 illustrates an inspection apparatus for a TFT substrate according to an embodiment of the present general inventive concept. As illustrated in FIG. 1, the inspection apparatus comprises a TFT substrate 10, a reference substrate 20, a power supply 40, an electron beam emitter 30, an electron beam detector 50, and a controller 60.

The reference substrate 20 is opposite to and spaced from the TFT substrate 10. Here, the reference substrate 20 is formed with a plurality of reference patterns 21 corresponding to a plurality of pixels 11 formed on the TFT substrate 10.

The power supply 40 is controlled by the controller 60 to supply power to both the pixel 11 of the TFT substrate 10 and the reference pattern 21 of the reference substrate 20. Here, when the power is supplied from the power supply 40 to the pixel 11 of the TFT substrate 10 and the reference pattern 21 of the reference substrate 10, an electric field is formed in a space between the TFT substrate 10 and the reference substrate 20.

Further, the power supply 40 is controlled by the controller 60 to supply the power to the reference pattern 21 selected among the reference patterns on the reference substrate 20. The reference pattern 21 may be randomly selected from the reference patterns. A number of the reference patterns may be simultaneously selected.

The electron beam emitter 30 emits an electron beam to the space between the TFT substrate 10 and the reference substrate 20, thereby allowing the electron beam to travel from a first side to a second side of the space between the TFT substrate 10 and the reference substrate 20.

Figure 2:
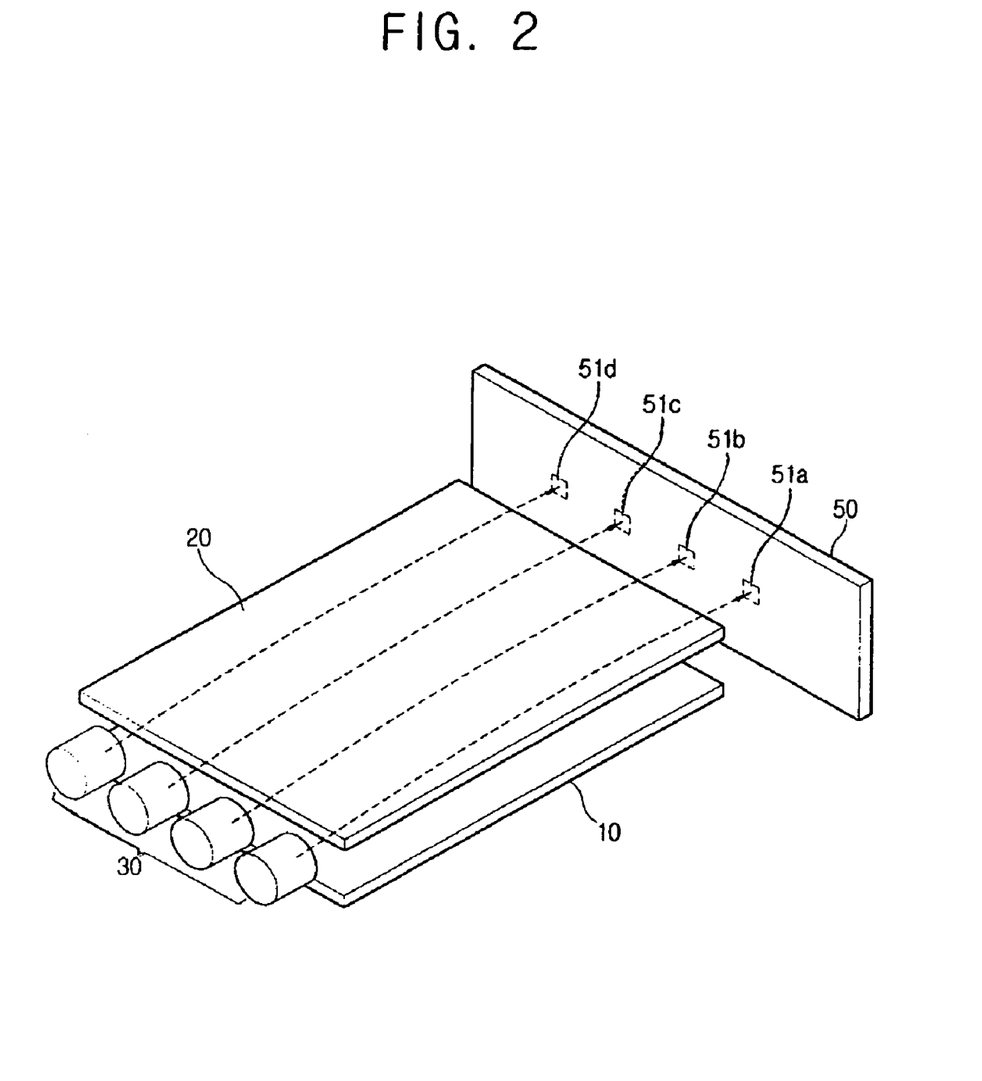
FIGS. 2 and 3 illustrate an electron beam emitter and an electron beam detector in the inspection apparatus of FIG. 1.
Figure 3:
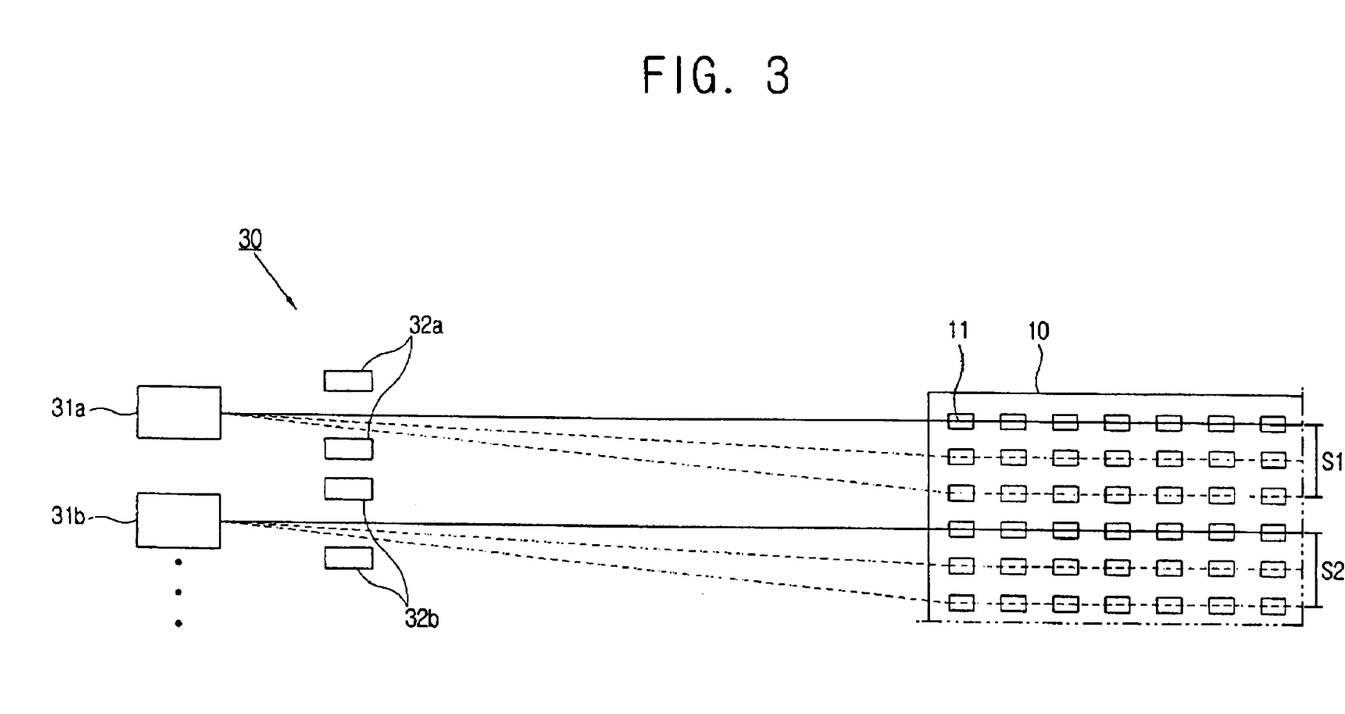

FIGS. 2 and 3 illustrate the electron beam emitter 30 and the electron beam detector 50 of the inspection apparatus of FIG. 1. Referring to FIGS. 1 through 3, the electron beam emitter 30 comprises a plurality of micro electron guns 31a and 31b, and a plurality of focusing units 32a and 32b respectively corresponding to the micro electron guns 31a and 31b.

The micro electron guns 31a and 31b are arranged on first side of the space to emit electron beams along a surface of the TFT substrate 10. The electron beam emitted from each micro electron gun 31a and 31b passes from the first side to the second side of the space between the TFT substrate 10 and the reference substrate 20, and is detected by the electron beam detector 50. In FIG. 2, the electron beam emitter 30 comprises four micro electron guns, but the number of micro electron guns is not limited to four.

Further, the electron beams emitted from the micro electron guns 31a and 31b are focused by the focusing units 32a and 32b, thereby assigning predetermined scan regions S1 and S2 to the electron guns 31a and 31b, respectively. Referring to FIG. 3, the electron beam emitted from each micro electron gun 31a or 31b is deflected at a predetermined angle, and passes between a predetermined pixel line of the TFT substrate 10 and a reference pattern line of the reference substrate 20 corresponding to the pixel line. Here, the respective scan regions S1 and S2 of the electron guns 31a and 31b are determined according to the deflected angles of the electron beams, so that the defect of the pixel 11 is inspected corresponding to each scan region S1 or S2.

The electron beam detector 50 is disposed opposite to the electron beam emitter 30 with respect to the TFT substrate 10 and the space which corresponds to a size of the TFT substrate 10 and the reference substrate 20. According to an embodiment of the present general inventive concept, the electron beam detector 50 is shaped like a plate perpendicular to the pixel line of the surface of the TFT substrate 10.

Further, the electron beam detector 50 includes a plurality of detectors 51a, 51b, 51c and 51d formed thereon to detect the electron beams emitted from the respective micro electron guns 31a and 31b.

The controller 60 determines whether the pixel 11 of the TFT substrate 10 has one of more defects, based on a detected location of the electron beam detected by the electron beam detector 50.

Figure 4:
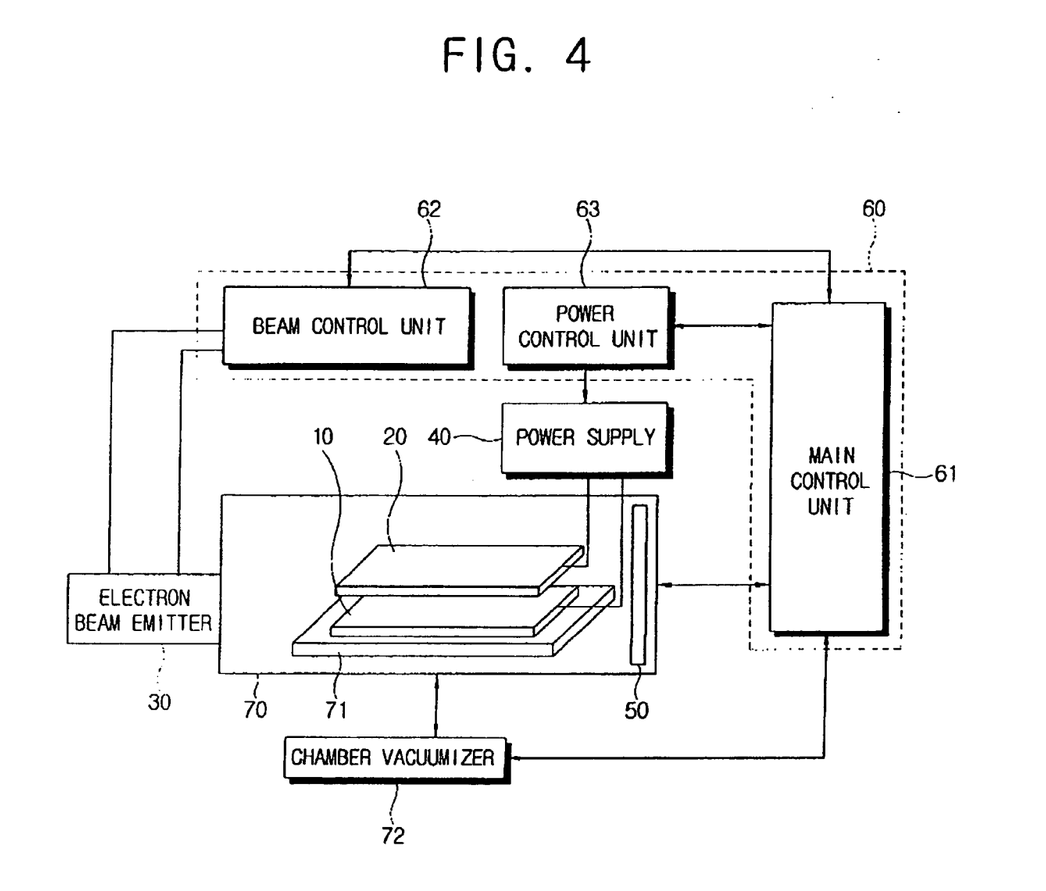
FIG. 4 illustrates detailed configurations of the inspection apparatus of FIG. 1.

As shown in FIG. 4, the controller 60 comprises a beam control unit 62, a power control unit 63, and a main control unit 61.

The beam control unit 62 is associated with the main control unit 61 to control each micro electron gun 31a or 31b of the electron beam emitter 30 to emit the electron beam and each focusing unit 32a or 32b to deflect the electron beam at a predetermined angle.

The power control unit 63 is associated with the main control unit 61 to control the power supply 40. Thus, it is possible to control the voltage and/or the supply of the power for the TFT substrate 10 and the reference substrate 20. Further, the power control unit 63 controls the power supply 40 to supply the power to at least one of the reference patterns 21 formed on the reference substrate 20.

The main control unit 61 determines whether the TFT substrate 10 has one or more defects, based on the detected location of the electron beam detected by the electron beam detector 50.

Hereinafter, it will be described how the main control unit 61 is associated with the beam control unit 62 and the power control unit 63 and determines whether the pixel 11 of the TFT substrate 10 has the one or more defects.

First, the main control unit 61 selects a predetermined pixel line of the TFT substrate 10. Here, the main control unit 61 can select a plurality of pixel lines corresponding to the scan regions S1 and S2 of the respective micro electron guns 31a and 31b so that the selected pixel lines corresponding to the micro electron guns 31a and 31b can be inspected at the same time. Further, the main control unit 61 can selectively inspect one or more pixel lines.

Then, information about the one or more pixel lines selected by the main control unit 61 is transmitted to the power control unit 63 and the beam control unit 62.

The beam control unit 62 controls the micro electron guns 31a and 31b and the focusing units 32a and 32b so that the electron beam passes through the space between the pixel line selected by the main control unit 61 and the reference pattern line corresponding to the selected pixel line.

Further, the power control unit 63 controls the power supply 40 to supply the power to the reference pattern line corresponding to the pixel line selected by the main control unit 61. At this time, the power control unit 63 can control the power supply 40 to supply the power to all pixels 11 of the TFT substrate 10 while the TFT substrate 10 is inspected. Thus, an electric field is applied between the reference substrate 20 and the TFT substrate 10. Here, when the power is not supplied to the reference pattern lines corresponding to the pixel lines unselected by the main control unit 61, the electric field is not formed between the unselected pixel line and the reference pattern line corresponding thereto.

In the meantime, while passing through the space between the TFT substrate 10 and the reference substrate 20, the electron beams emitted from the micro electron guns 31a and 31b are deflected by the electric fields formed in the space. Then, the deflected electron beam is detected at a predetermined location of the electron beam detector 50.

Then, the main control unit 61 determines whether the corresponding pixel line has a defective pixel 11, based on the detected location of the electron beam detected by the electron beam detector 50.

Figure 5:
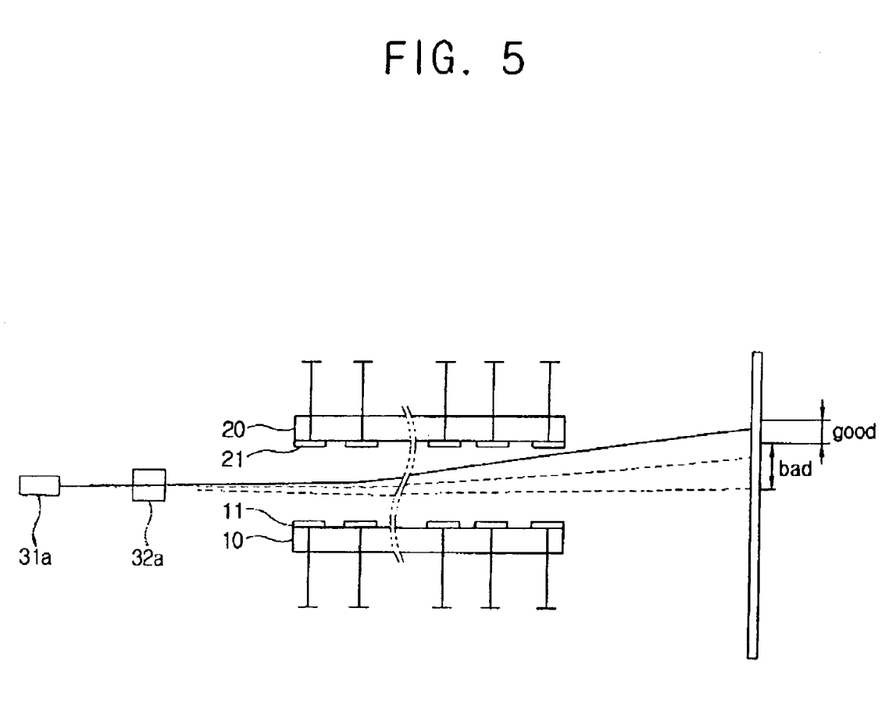
FIG. 5 illustrates a method of determining whether a TFT substrate has a defect using deflection of an electron beam in an inspection apparatus according to an embodiment of the present general inventive concept.

For example, as illustrated in FIG. 5 the main control unit 61 determines whether the corresponding pixel line has a defective pixel 11, based on the detected location of the deflected electron beam by the electron beam detector 50.

First, the main control unit 61 previously stores information about the location of the electron beam detected by the electron beam detector 50 when the selected pixel line has no defective pixel, i.e., information about a reference detection location. Here, the reference detecting location can be obtained by experiments or calculated based on the electric field, the electrons speed, the distance between the inspected pixel 11 and the electron beam detector 50, etc.

Further, the main control unit 61 compares the reference detection location with the actual detected location of the electron beam passing through the selected pixel line and detected by the electron beam detector 50. The main control unit 61 determines that the selected pixel line has no defective pixel when the detected location is matched with the reference detection location (or belongs to a predetermined detecting area).

On the other hand, the main control unit 61 determines that the selected pixel line has at least one defective pixel 11 when the detected location is deviated from the reference detection location.

Through the foregoing method, the main control unit 61 detects the pixel line having the defective pixel 11 among all pixel lines of the TFT substrate 10.

Meanwhile, the main control unit 61 detects the defective pixel 11 from the pixel line, as follows. Here, the pixel line having the defective pixel 11 will be called a defective pixel line.

The main control unit 61 selects the reference pattern 21 to receive the power in the reference pattern line of the reference substrate 20 corresponding to the defective pixel line, based on the detected location of the electron beam passing through the defective pixel line. For example, the main control unit 61 determines an approximate location of the defective pixel 11 in the defective pixel line based on the deviation of the detected location from the reference detecting location. Here, the location of the defective pixel 11 in the defective pixel line is obtained by experiments or calculated based on the electric field, the electron beam deflection, etc. For example, the reference pixel line can be divided into two pixel groups that belong to the electron beam emitter side and the electron beam detector side based on the deviation of the detected location from the reference detection location.

When the main control unit 61 determines that the defective pixel 11 is located in the pixel group of the electron beam emitter side on the basis of the deviated degree of the detected location from the reference detecting location, the main control unit 61 informs the power control unit 63 and the beam control unit 62 that the defective pixel 11 is located in the pixel group of the electron beam emitter side.

At this time, the power control unit 63 supplies the power to only the reference pattern 21 corresponding to the pixel 11 that belongs to the pixel group determined by the main control unit 61. Further, the beam control unit 62 controls the electron beam emitter 30 to pass the electron beam through the pixel group determined by the main control unit 61.

Here, the main control unit 61 has previously stored information about the location of the electron beam detected by the electron beam detector 50 when the determined pixel group includes no defective pixel 11, i.e., information about the reference detection location for the determined pixel group. Here, the reference detecting location for the determined pixel group can be obtained by experiments or calculated on the basis of the electric field, the electron beam deflection, etc.

Further, the main control unit 61 compares the reference detection location for the determined pixel group with the detected location of the electron beam passing through the determined pixel group and detected by the electron beam detector 50. Then the main control unit 61 determines what pixel of the determined pixel group has defects according to whether the detected location is matched with the reference detection location for the determined pixel group (or belongs to a predetermined detecting area).

Here, the main control unit 61 determines an approximate location of the defective pixel 11 in the determined pixel group based on the basis of the deviation of the detected location from the reference detection location for the determined pixel group, thereby finally detecting the defective pixel 11.

Referring to FIGS. 1 and 4, the inspection apparatus comprises a substrate stage 71 on which the TFT substrate 10 is put to be opposite to and spaced from the reference substrate 20, a vacuum chamber 70 to accommodate the reference substrate 20, the electron beam detector 50 and the substrate stage 71, and a chamber vacuumizer 72 to vacummize the vacuum chamber 70 according to control of the controller 60.

While the TFT substrate 10 is inspected, the controller 60 controls the chamber vacuumizer 72 to maintain the vacuum chamber 70 in a lower vacuum state than that of the conventional inspection apparatus. Contrary to the conventional inspection apparatus that requires the vacuum chamber to have a higher vacuum state for more correctly detecting the secondary electrons, the inspection apparatus according to an embodiment of the present general inventive concept correctly determines whether the TFT substrate 10 is defective or not based on the electron beam deflection even though the vacuum chamber 70 thereof is in a lower vacuum state than that of the conventional inspection apparatus. As the vacuum chamber 70 is maintained in the lower vacuum state, it is possible to reduce the time taken to highly vaccumize the vacuum chamber 70, and simplify the configurations of the chamber vacuumizer 72.

Because electron beams are easily deflected by the focusing units to propagate along different lines in the space between the TFT substrate 10 and the reference substrate 20, substrates with different sizes can be easily inspected without additional adjustments of the electron beam emitter.

In the foregoing embodiment, the defective pixel line may be divided into two or more pixel groups so as to more accurately detect the defective pixel from the defective pixel line. Alternatively, various algorithms using multiple experiments or the minimum measurement based on calculation considering the electric field and the electron beam deflection may be used in detecting the position of defective pixel.

As described above, the present general inventive concept provides an inspection apparatus capable of correctly and quickly inspecting a TFT substrate for defects in a low vacuum state regardless the size of the TFT substrate.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

What is claimed is:

1. An inspection apparatus for a TFT substrate formed with a plurality of pixels, comprising:
    a reference substrate spaced apart from the TFT substrate and formed with a plurality of reference patterns corresponding to the pixels;
    a power supply to supply power to both a predetermined number of the plurality of pixels and at least one of the reference patterns corresponding to the predetermined number of the plurality of pixels to form an electric field in a space between the TFT substrate and the reference substrate;
    an electron beam emitter to emit an electron beam to travel from a first side to a second side of the space;
    an electron beam detector to detect the electron beam emitted from the electron beam emitter after passing through the space; and
    a controller to determine whether the TFT substrate includes a defective pixel based on a location of the electron beam detected by the electron beam detector.

2. The inspection apparatus according to claim 1, wherein:
    the electron beam emitter comprises a plurality of micro electron guns arranged on the first side of the space along a surface of the TFT substrate to respectively emit electron beams, and a plurality of focusing units to focus the electron beams emitted from the corresponding micro electron guns; and the controller controls the focusing units to focus the electron beams emitted from the respective micro electron guns to pass between at least one pixel line formed by a predetermined number of the plurality of pixels of the TFT substrate and at least one reference line of the reference patterns corresponding to the pixel line.

3. The inspection apparatus according to claim 2, wherein the controller controls the power supply to selectively supply power to the at least one reference line of the plurality of reference patterns of the reference substrate.

4. The inspection apparatus according to claim 3, wherein the controller has information about a reference detection location when the TFT substrate includes no defective pixel, and determines whether the TFT substrate includes the defective pixel based on a deviation between the reference detection location and the location of the electron beam detected by the electron beam detector.

5. The inspection apparatus according to claim 1, further comprising:
    a substrate stage on which the TFT substrate is placed to be opposite to and spaced from the reference substrate;
    a vacuum chamber to accommodate the reference substrate, the electron beam detector and the substrate stage; and
    a chamber vacuumizer to vacummize the vacuum chamber according to control of the controller.

6. An inspection apparatus to identify a defect on a TFT substrate, comprising:
    an electron beam emitter to emit at least one electron beam toward a space between the TFT substrate and a reference substrate; and
    an electron beam detector to detect a location of the at least one electron beam passing through the space and to detect a defective pixel of the TFT substrate according to the detected location of the at least one electron beam.

7. The apparatus according to claim 6, further comprising:
    a power supply to supply a power to the TFT substrate and the reference substrate to form an electric field to control the at least one electron beam to pass through a passage in the space.

8. The inspection apparatus according to claim 7, further comprising:
    a controller to select first pixels of the TFT substrate as a pixel line and second pixels of the reference substrate as a reference line,
    wherein the power supply supplies the power to the first pixels and the second pixels.

9. The inspection apparatus according to claim 7, wherein the electric field causes the at least one electron beam to be deflected in the space, and an amount of deflection varies according to the defective pixel.

10. The inspection apparatus according to claim 6, wherein the TFT substrate comprises pixel lines having pixels, the reference substrate comprises reference lines corresponding to the respective pixel lines, and the electron beam emitter emits the at least one electron beam along the space between one of the pixel lines and one of the reference lines corresponding to the one of the pixel lines.

11. The inspection apparatus according to claim 10, further comprising:
    a power supply to supply a power to the one of the pixel lines to form an electric field to control a passage of the at least one electron beam.

12. The inspection apparatus according to claim 11, wherein the location of the at least one electron beam comprises a first location detected when the one of the pixel lines of the TFT substrate does not include the defective pixel, and a second location detected when the one of the pixel lines of the TFT substrate includes the defective pixel.

13. The inspection apparatus according to claim 12, wherein the first location and the second location are different from each other in a direction perpendicular to a surface of the TFT substrate.

14. The inspection apparatus according to claim 12, further comprising:
a controller to select the defective pixel according to a difference between the first location and the second location.

15. The inspection apparatus according to claim 11, wherein the defective pixel comprises a first number of pixels and a second number of pixels, the location of at least one electron beam comprises a first location detected when one of the pixel lines of the TFT substrate does not include the first and second number of pixels, and a second location detected when the one of the pixel lines of the TFT substrate include one of the first number of pixel and the second number of pixels.

16. The inspection apparatus according to claim 15, further comprising:
a controller to detect one of the first number of pixels and the second number of pixels according to a difference between the first location and the second location.

17. The inspection apparatus according to claim 6, further comprising:
at least one focusing unit corresponding to the at least one electron beam to direct the corresponding electron beam in the space.

18. The inspection apparatus according to claim 6, further comprising:
a vacuum chamber enclosing the electron beam detector, the TFT substrate and the reference substrate.

19. The inspection apparatus according to claim 6, wherein two or more defective pixels of the TFT substrate are identified according to the detected location of the at least one electron beam.

20. A method of identifying a defect on a TFT substrate using an electron beam in an inspection apparatus, the method comprising:
supplying an electric field between a pixel line of the TFT substrate and a reference line of a reference substrate;
directing the electron beam along the electric field;
detecting a location of the electron beam after passing along the electric field through a space between the TFT substrate and the reference substrate; and
identifying a defect on the TFT substrate based on a deviation of the detected location from a reference detection location.

* * * * *